US009867863B2

(12) United States Patent
Chawla

(10) Patent No.: US 9,867,863 B2
(45) Date of Patent: Jan. 16, 2018

(54) METHOD OF TREATING LOW BLOOD PRESSURE

(71) Applicant: The George Washington University a Congressionally Chartered Not-for-Profit Corporation, Washington, DC (US)

(72) Inventor: Lakhmir Chawla, McLean, VA (US)

(73) Assignee: The George Washington University a Congressionally Chartered Not-for-Profit Corporation, Washington, DC (US)

(*) Notice: Subject to any disclaimer, the term of this patent is extended or adjusted under 35 U.S.C. 154(b) by 0 days.

(21) Appl. No.: 15/380,574

(22) Filed: Dec. 15, 2016

(65) Prior Publication Data
US 2017/0095526 A1 Apr. 6, 2017

Related U.S. Application Data

(63) Continuation of application No. 12/639,987, filed on Dec. 16, 2009, now Pat. No. 9,572,856.

(51) Int. Cl.
*A61K 38/08* (2006.01)

(52) U.S. Cl.
CPC .................................. *A61K 38/085* (2013.01)

(58) Field of Classification Search
None
See application file for complete search history.

(56) References Cited

U.S. PATENT DOCUMENTS

| 4,330,532 | A | 5/1982 | Nyeki et al. |
| 5,216,025 | A | 6/1993 | Gross et al. |
| 5,444,067 | A | 8/1995 | Kivlighn et al. |
| 6,592,865 | B2 | 7/2003 | Parry et al. |
| 7,666,408 | B2 | 2/2010 | Bachmann |
| 2011/0144026 | A1 | 6/2011 | Chawla |

FOREIGN PATENT DOCUMENTS

WO   WO-2015/095535 A1   6/2015

OTHER PUBLICATIONS

Griffin, Hypertension 1991;17:626-635.*
Kakavas et al., "Vasoactive support in the optimization of post-cardiac arrest hemodynamic status: From pharmacology to clinical practice," European Journal of Pharmacology 667 (2011), pp. 34-40.
Morrell et al., "The Management of Severe Sepsis and Septic Shock," Infect. Dis. Clin. N. Am. 23 (2009) pp. 485-501.
Lata et al., "Hepatorenal syndrome," World Journal of Gatroenterology, 2012, 18936: 4978-4984.
Bacgenm, "Angiotensin II acetate salt," http://shop.bachem.com/h-1705.html (Mar. 31, 2017).
Eriksson et al., "Just the Beginning: Novel Functions for Angiotensin-Converting Enzymes," Current Biology, Vo. 12, R745-752 (Oct. 29, 2012).
Le et al., "Angiotensin IV is a Potent Agonist for Contitutive Active Human AT1 Receptors," The Journal of Biological Chemistry, Vo. 277, No. 26, pp. 23107-23110 (2002).
Lee et al., "34-Year-Old Woman With Hypotension, Respiratory Failure, Fever, and an Abdominal Mass," West J Med, 158: 499-505 (1993).
Unknown Author, "NSC107678," http://www.repository.cam.ac.uk/handle/1810/88629 (Jun. 21, 2017).
O'Brien et al., "Terlipressin for norepinephrine-resistant septic shock," Research Letters, The Lancelet, vol. 359, pp. 1209-1210 (2002).
Simon et al., "Duration and magnitude of hypotension and monocyte deactivation in patients with community-acquired pneumonia," Shock, 36(6), pp. 553-559 (Dec. 2011).
Tremblay et al., "Effect of Hypotension Preceding Death on the Function of Lungs from Donors with Nonbeating Hearts," The Journal of Heart and Lung Transplantation, vol. 15, No. 3, pp. 260-268 (1996).
Weisgerber et al., "Vasopressin analogue injection as ultimate measure for counteracting severe catecholamine-refractory poisoning by several vasodilators taken with suicidal intent," Dtsch Med Wochenschr, pp. 2189-5192 (2003).
Ames et al., "Prolonged Infusions of Angiotensin II and Norepinephrine and Blood Pressure, Electrolyte Balance, and Aldosterone and Cortisol Secretion in Normal Man and in Cirrhosis and Ascites," Journal of Clinical Investigation, 1965; 44(7): 1171-1186.
Angus et al., Epidemiology of severe sepsis in the United States: Analysis of incidence, outcome, and associated costs of care. Crit Care Med 29:1303-1310, 2001.
Avanzini et al., Journal of Hypertension, 2006, vol. 24, No. 12, 2377-2385.
Bagshaw et al., A Multi-Centre Evaluation of the Rifle Criteria for Early Acute Kidney Injury in Critically Ill Patients. Nephrol Dial Transplant Oct. 25 (Epub): 2007.
Basso et al., History about the discovery of the renin-angiotensin system. *Hypertension* 2001, 38(6):1246-1249.
Busse et al., P160 "Angiotensin II may be used for the treatment of hypotension in distributive shock, but a safe and efficacious dose is unknown", Critical Care 2014, vol. 18, Supp11, http://ccforum.com/supplements/18/51, p. S57.
Campbell, D.J., "Do intravenous and subcutaneous angiotensin II increase blood pressure by different mechanisms?," Frontiers in Research Review: Evolving Concepts of the Renin-Angiotensin System, Clinical and Experimental Pharmacology and Physiology, 40, 560-570, 2013.
Chawla, L.S. et al., "Intravenous Angiotensin II for the Treatment of Hihg-output Shock (ATIIOS trial): A Pilot Study," Critical Care, vol. 18, Issue 5, Article No. 534, published on-line Oct. 6, 2014.
Cohn, J., et al., "Studies in Clinical Shock and Hypotension. II. Hemodynamic Effects of Norepinephrine and Angiotensin," Journal of Clinical Investigation, vol. 44, No. 9, pp. 1494-1504, 1965.

(Continued)

*Primary Examiner* — Satyanarayana R Gudibande
(74) *Attorney, Agent, or Firm* — Venable LLP; Henry J. Daley; Annette K. Kwok

(57) ABSTRACT

A method for treating a patient suffering from one of septic shock, acute kidney injury, severe hypotension, cardiac arrest, and refractory hypotension, but not from myocardial infarction, is provided. The method includes administering a therapeutically effective dose of Angiotensin II, or Ang II, to the patient.

28 Claims, No Drawings

(56) References Cited

OTHER PUBLICATIONS

Corrêa, T.D. MD, et al., "Angiotensin II in Septic Shock: Effects on Tissue Perfusion, Organ Function, and Mitochondrial Respiration in a Porcine Model of Fecal Peritonitis," Clinical Care Mediine, vol. 42, No. 8, pp. e550-e559, 2014.
Daskalopoulos et al., "Effects of captopril on renal function in patients with cirrhosis and ascites," Journal of Hepatology, 1987; 4: 330-336.
Del Greco, F.D. MD, et al., "Clinical Experience with Angiotensin II in the Treatment of Shock," J.A.M.A., vol. 178, No. 10, pp. 130-135, 1961.
Dellinger, R.P. et al., "Surviving Sepsis Campaign: International Guidelines for Management of Severe Sepsis and Septic Shock: 2012," Critical Care Medicine, vol. 41, No. 2, pp. 580-657, 2013.
Downing, S.E. "Effects of Angiotensin II and Norepinephrine on Ventricular Performance During, Oligemic Shock," The Yale Journal of Biology and Medicine, Inc., vol. 36, pp. 407-420, 1964.
Dworkin, Br. J. Cancer 71, 942-944, 1995.
Gines et al., "Hepatorenal syndrome," Lancet, 2003; 362(9398): 1819-1827.
Goldsmith et al., Effect of a pressor infusion of angiotensin II on sympathetic activity and heart rate in normal humans. Ciro Res 1991, 68(1):263-268.
Harrison-Bernard, L.M., The renal renin-angiotensin system. Adv Physiol Educ, (2009) 33(4): p. 270-74.
Helmy et al., "Nitric oxide mediates the reduced vasoconstrictor response to angiotensin II in patients with preascitic cirrhosis," Journal of Hepatology, 2003; 38: 44-50.
Heringlake et al., Renal dysfunction according to the ADQI-RIFLE system and clinical practice patterns after cardiac surgery in Germany. Minerva Anestesiol 72:645-654, 2006.
Jackson et al., Enalapril overdose treated with angiotensin infusion. Lancet 1993, 341(8846):703.
Kanaparthi et al., Distributive Shock, Medscape Reference, Feb. 13, 2013.
Kopacova et al., "Hepatorenal syndrome," World Journal of Gastroenterology, 2012; 18(36): 4978-4984.
Kuitunen et al., Acute renal failure after cardiac surgery: evaluation of the RIFLE classification. Ann Thorac Surg 81:542-546, 2006.
LaGrange et al., Hypertension, 2003; 42:1124-1129.
Laragh et al., "Angiotensin II, Norepinephrine, and Renal Transport of Electrolytes and Water in Normal Man and in Cirrhosis with Ascites," Journal of Clinical Investigation, 1963; 42(7): 1179-1192.
Li, T. et al., "Changes in Sensitivity of Vascular Smooth Muscle to Calcium and Its Role in the Biphasic Change in Vascular Reactivity Following Hemorrhagic Shock in Rats," Chinese Critical Care Medicine, vol. 17, No. 11, pp. 647-650, Nov. 2005, English Abstract only.
Lianos et al., "Angiotensin-induced sodium excretion patterns in cirrhosis: Role of renal prostaglandins," Kidney International, 1982; 21: 70-77.
Lopes et al., Prognostic utility of RIFLE for acute renal failure in patients with sepsis. Crit Care 11:408, 2007.
Mayo Clinic, Septis Symptoms-Mayo Clinic, accessed on Jun. 12, 2015, available online at: http://www.mayoclinic.org/diseases-conditions/sepsis/basics/symptoms/con-20031900.
McCloy et al., "Angiotensis-induced Natriuresis in Cirrhosis in the Absence of Endogenous Aldosterone Secretion," Ann Intern Med. 1966, 64(6): 1271-1276.
Morelli et al., Singer M: Effect of heart rate control with esmolol on hemodynamic and clinical outcomes in patients with septic shock: a randomized clinical trial. JAMA 2013, 310(16):1683-1691.
Myburgh et al., CAT Study investigators: A comparison of epinephrine and norepinephrine in critically ill patients. Intensive Care Med 2008, 34(12):2226-2234.

Nassif, A.C. et al., "Angiotensin II in Treatment of Hypotensive States," J.A.M.A. vol. 183, No. 9, pp. 751-754, 1963.
Newby D.E. et al., "Enalapril overdose and the corrective effect of intravenous angiotensin II," Br. J. Clin Pharmacol, vol. 40, pp. 103-104, 1995.
Newby et al., "Peripheral vascular tone in patients with cirrhosis: role of the renin-angiotensin and sympathetic nervous systems," Cardiovascular Research, 1998; 38: 221-228.
Niu, C.Y. et al., "Lymphatic Hyporeactivity and Calcium Desensitization Following Hemorrhagic Shock," Shock, vol. 37, No. 4, pp. 415-423, Apr. 2012.
Page, I.H. et al., "Angiotensin," Physiological , vol. 41, pp. 331-390, 1961.
Rona G: Catecholamine cardiotoxicity. J Mol Cell Cardiol 1985, 17(4):291-306.
Rose, J. MD, et al., "Comprison of Effects of Angiotensin and Norepinephrine on Pulmonary Circulation, Systemic Arteries and Veins, and Systemic Vascular Capacity in the Dog," Circulation, vol. 25, pp. 247-252, 1962.
Russell et al., VASST Investigators: Vasopressin versus norepinephrine infusion in patients with septic shock. N Engl J Med 2008, 358(9):877-887.
Ryding, J. et al., "Reversal of 'Refractory Septic Shock' vby Infusion of Amrinone and Angiotensin II an Anthracycline-Treated Patient," Chest, 107, 201-203, 1995.
Salerno et al., "Diagnosis, Prevention and Treatment of Hepatorenal Syndrome in Cirrhosis," Recent Advanced in Clinical Practice GUT , 2007; 56: 1310-1318.
Sansoe et al., "Inappropriately low angiotensin II generation: a factor determining reduced kidney function and survival in patient with decompensated cirrhosis," 2004; 40: 417-423.
Schroeder et al., "Renal Failure in Patients with Cirrhosis of the Liver," Am J Med, 1967; 43(6): 887-96.
Struthers et al., Review of aldosterone- and angiotensin II-induced target organ damage and prevention. Cardiovasc Res 2004, 61(4):663-670.
Thomas, V.L. et al., "Administration of Angiotensin II in refractory septic shock," Critical Care Medicine, vol. 19, No. 8, pp. 1084-1086, 1991.
Trilli et al., Lisinopril overdose and management with intravenous angiotensin II. Ann Pharmacother 1994, 28(10):1165-1168.
Uchino et al., Acute renal failure in critically ill patients: a multinational, multicenter study. JAMA 294:813-818, 2005.
Vaile, J.C. et al., "Angiotensin II modulates cardiovascular autonomic control in the absence of baroreflex loading," Heart, vol. 80, pp. 127-133, 1998.
Vincent et al., The SOFA (Sepsis-related Organ Failure Assessment) score to describe organ dysfunction/failure. On behalf of the Working Group on Sepsis-Related Problems of the European Society of Intensive Care Medicine. Intensive Care Med 1996, 22(7):707-710.
Vincent JL, De Backer D: Circulatory shock. N Engl J Med 2013, 369(18):1726-1734.
Walpole et al., BMC Public Health, 2012, 12:439.
Wan, L. et al., "Angiotensin II in experimental hyperdynamic sepsis," Critical Care vol. 13, No. 6, pp. 1-10, 2009.
Whiteley et al., Treatment of hypotension in septic shock. Lancet 1996, 347(9001):622.
Wilson et al., U.S. trends in CABG hospital volume: the effect of adding cardiac surgery programs. Health Aff 26:162-168, 2007.
Wray, G.M. et al., "Severe septic shock unresponsive to nonadrenaline," Lancet vol. 346, p. 1604, 1995.
Wray, G.M. et al., "Severe septic shock unresponsive to noradrenaline," Lancet vol. 346, p. 1604, 1995.
Yunge M. et al., "Angiotensin for septic shock unresponsive to noradrenaline," Arch Dis Child 2000, Vo. 82, pp. 388-389, 2014.
Ziegler et al., "Hepatorenal Syndrome: A Disease Mediated by the Intrarenal Action of Renin," Med Hypothesis, 1976; 2: 15-213.

* cited by examiner

METHOD OF TREATING LOW BLOOD PRESSURE

CROSS-REFERENCE TO RELATED APPLICATIONS

This patent application is a continuation of U.S. application Ser. No. 12/639,987, filed on Dec. 16, 2009, the entire content of which is hereby incorporated by reference.

FIELD OF THE INVENTION

The present teachings relate to a therapeutic regimen for patients suffering from at least one of septic shock, acute kidney injury, severe hypotension, cardiac arrest, and refractory hypotension.

BACKGROUND OF THE INVENTION

Severe sepsis is the leading cause of acute kidney injury ("AKI") and its incidence is increasing.

The two leading clinical conditions associated with AKI are sepsis and cardiac surgery. In the largest epidemiologic study to date (>120,000), Bagshaw et al. found that AKI occurred in 36% of intensive care unit patients and that the most common primary diagnosis was sepsis. Similarly, in a large international observational study of AKI requiring renal replacement therapy (RRT), approximately 50% of subjects had sepsis. Direct comparisons of incidence of AKI arising from sepsis vs. cardiac surgery have not been made but two studies in cardiac surgery found incidence rates of 16% and 19% while the incidence in patients with sepsis was twice as great. Furthermore, while the rates of cardiac surgery are steadily declining, sepsis incidence continues to climb. Severe sepsis currently affects more than 750,000 Americans each year and the incidence rises exponentially with age, suggesting that the number of cases will rise in coming years as baby boomers age.

Patients with septic shock who require high dose vasopressors have a mortality of over 80%. Currently, no specific type of vasopressor (e.g. norepinephrine, vasopressin, dopamine) has been shown to improve outcome. Importantly, patients on high dose catecholamines (e.g., dopamine, epinephrine, norepinephrine) for septic shock often develop tachyphylaxis, limiting the utility of these agents in the sickest patients. Vasopressin, which has been used as an adjuvant with cathecholamines, has not been shown to improve outcomes in patients with septic shock. In the subset of patients whose mean arterial pressure cannot be maintained with current vasopressors, septic shock is uniformly fatal.

Accordingly, there exists a need for the addition of an effective drug for the treatment of hypotension that does not have the deleterious effects of the present range of treatments.

SUMMARY OF THE INVENTION

The present teachings disclose a method of treating a patient suffering from low blood pressure.

According to an embodiment of the present teachings, a method of treating a patient suffering from low blood pressure is provided. The patient can suffer from one of septic shock, acute kidney injury, severe hypotension, and refractory hypotension, but not from myocardial infarction. The method can comprise administering a therapeutically effective dose of Angiotensin II ("Ang II") to the patient.

The dose of Angiotensin II can be administered at a rate of between about 5 ng/kg/min to about 100 ng/kg/min. The dose of Angiotensin II can be administered at a rate of between about 10 ng/kg/min to about 50 ng/kg/min. The dose of Angiotensin II can be administered at a rate of between about 20 ng/kg/min to about 40 ng/kg/min.

The dose administration can last from about 0.25 hours to about 120 hours. The dose administration can last from about 1 hour to about 7 hours. The dose administration can last from about 2 hour to about 6 hours. The dose administration can last from about 3 hours to about 5 hours.

Additional features and advantages of various embodiments will be set forth, in part, in the description that follows, and, in part, will be apparent from the description, or may be learned by practice of various embodiments. The objectives and other advantages of various embodiments will be realized and attained by means of the elements and combinations particularly pointed out in the description herein.

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

Ang II is degraded to angiotensin III in a patient, having a half life of a few minutes. Ang II is a direct vasoconstrictor by activating angiotensin I receptors, enhancing peripheral noradrenergic neurotransmission, increasing sympathetic discharge (CNS), and releasing catecholamines from the adrenal medulla.

Administration of Ang II to patients suffering from at least one of septic shock, acute kidney injury, severe hypotension, cardiac arrest, and refractory hypotension can have adverse side effects, including ischemia, such as, for example, mesenteric ischemia, that damage internal organs. The present teachings disclose a therapeutic regimen of Ang II at doses below that where adverse side effects, such as ischemia, are seen. Furthermore, the therapeutic regimen of Ang II disclosed in the present teachings can act as an adjuvant and lower the effective doses of other therapies, including administration of vasopressin and catecholamine.

The therapeutic regimen disclosed herein can be started within, for example, 1 hour, 2 hours, 4 hours, 6 hours, or 12 hours after onset of acute symptoms.

Example I

A dose study was designed to determine the feasibility of Ang II as a treatment for sepsis related hypotension.

A 20 patient randomized blinded study in the treatment of sepsis related hypotension was proposed. Patients suffering from septic shock receiving >15 mcg/min of norepineprhine are eligible. Patients are randomized to Ang II or norepinephrine in a blinded fashion. There are 10 patients in each arm. Norepinephrine is used as a control instead of a true placebo, because the blood pressure rising effects of Ang II would defeat the blinding intent.

All patients have the treatment of vasopressors titrated to a mean arterial pressure (MAP) of 65 mm of Hg. Patients are then randomized to a control group or arm, or an interventional group or arm treated with Ang II. Patients randomly assigned to the control group are administered with norepinephrine starting at 5 mcg/min, and can be titrated up to 7.5 mcg/mink, and then to 10 mcg/min. Patients in the interventional arm are administered Ang II starting at a dose of about 2 Ong/kg/min. Additionally, the dose can then be titrated up to about 30 ng/kg/min. Furthermore, the dose can then be titrated up to about 40 ng/kg/min. The intervention can last for about 4 hours.

Each patient in the interventional group is started with the assigned starting dose. After the first hour, if the patient is still requiring standing norepinephrine, the dose of the control and interventional drugs can be increased 50%. After the second hour, if the patient is still requiring a standing dose of norepinephrine, the control and interventional drugs can be increased again to twice the initial dose. At the end of 4 hours, the study drug will be titrated off over 30 minutes.

In the two hours before the initiation of the study drug, all urine is collected. The urine collections are continued for a total duration of nine (9) hours. Blood is drawn at the initiation of the study, four (4) hours thereafter, and then seven (7) hours after. This involves a total of three (3) blood draws of 7 cc of blood per draw for a total of 21 cc of blood. Blood is examined for serum chemistry and serum lactate. In this same time period, demographic and clinical data are collected. Creatinine clearance will be calculated for the pre-study, study, and post-study periods.

Blood pressure of each patient is monitored continuously from about two (2) hours before initiation of the control and interventional drugs for about seven (7) hours after initiation of the control and interventional drugs.

Results:

At the conclusion of the study, 30 day mortality is assessed.

According to an embodiment of the present teachings, a method of treating a patient suffering from low blood pressure is provided. The patient can suffer from one of septic shock, acute kidney injury, severe hypotension, and refractory hypotension, but not from myocardial infarction. The method can comprise administering a therapeutically effective dose of Angiotensin II ("Ang II") to the patient.

The dose of Angiotensin II can be administered at a rate of between about 5 ng/kg/min to about 100 ng/kg/min. The dose of Angiotensin II can be administered at a rate of between about 10 ng/kg/min to about 50 ng/kg/min. The dose of Angiotensin II can be administered at a rate of between about 20 ng/kg/min to about 40 ng/kg/min.

The dose administration can last from about 0.25 hours to about 120 hours. The dose administration can last from about 1 hour to about 7 hours. The dose administration can last from about 2 hour to about 6 hours. The dose administration can last from about 3 hours to about 5 hours.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

The following publications are herein incorporated by reference in their entireties:

1. Bagshaw S M, George C, Dinu I, Bellomo R: A Multi-Centre Evaluation of the Rifle Criteria for Early Acute Kidney Injury in Critically Ill Patients. Nephrol Dial Transplant Oct. 25, 2007 (Epub):
2. Uchino S, Kellum J A, Bellomo R, Doig G S, Morimatsu H, Morgera S, Schetz M, Tan I, Bouman C, Macedo E, Gibney N, Tolwani A, Ronco C: Acute renal failure in critically ill patients: a multinational, multicenter study. JAMA 294:813-818, 2005
3. Heringlake M, Knappe M, Vargas H O, et al: Renal dysfunction according to the ADQI-RIFLE system and clinical practice patterns after cardiac surgery in Germany. Minerva Anestesiol 72:645-654, 2006
4. Kuitunen A, Vento A, Suojaranta-Ylinen R, Pettila V: Acute renal failure after cardiac surgery: evaluation of the RIFLE classification. Ann Thorac Surg 81:542-546, 2006
5. Lopes J A, Jorge S, Resina C, et al: Prognostic utility of RIFLE for acute renal failure in patients with sepsis. Crit Care 11:408, 2007
6. Wilson C T, Fisher E S, Welch H G, Siewers A E, Lucas F L: U.S. trends in CABG hospital volume: the effect of adding cardiac surgery programs. Health Aff 26:162-168, 2007
7. Angus D C, Linde-Zwirble W T, Lidicker J, Clermont G, Carcillo J, Pinsky M R: Epidemiology of severe sepsis in the United States: Analysis of incidence, outcome, and associated costs of care. Crit Care Med 29:1303-1310, 2001

What is claimed is:

1. A method of treating a human patient suffering from refractory hypotension, comprising administering angiotensin II to the patient at a rate of about 5 ng/kg/min to about 10 ng/kg/min while the patient is receiving a vasopressor, wherein the vasopressor is vasopressin or a catecholamine.

2. The method of claim 1, wherein the Angiotensin II is administered to the patient over a period of from about 1 hour to about 7 hours.

3. The method of claim 1, wherein the Angiotensin II is administered to the patient over a period of from about 2 hours to about 6 hours.

4. The method of claim 1, wherein the Angiotensin II is administered to the patient over a period of from about 3 hours to about 5 hours.

5. The method of claim 1, wherein the vasopressor is vasopressin.

6. The method of claim 1, wherein the vasopressor is a catecholamine.

7. The method of claim 6, wherein the catecholamine is norepinephrine.

8. The method of claim 7, wherein the norepinephrine is administered to the patient at a rate of >15 mcg/min.

9. The method of claim 1, wherein the rate of administration is about 5 ng/kg/min.

10. The method of claim 9, wherein the Angiotensin II is administered to the patient over a period of from about 1 hour to about 7 hours.

11. The method of claim 9, wherein the Angiotensin II is administered to the patient over a period of from about 2 hours to about 6 hours.

12. The method of claim 9, wherein the Angiotensin II is administered to the patient over a period of from about 3 hours to about 5 hours.

13. The method of claim 9, wherein the vasopressor is vasopressin.

14. The method of claim 9, wherein the vasopressor is a catecholamine.

15. The method of claim 1, wherein the rate of administration is about 10 ng/kg/min.

16. The method of claim 15, wherein the Angiotensin II is administered to the patient over a period of from about 1 hour to about 7 hours.

17. The method of claim 15, wherein the Angiotensin II is administered to the patient over a period of from about 2 hours to about 6 hours.

18. The method of claim 15, wherein the Angiotensin II is administered to the patient over a period of from about 3 hours to about 5 hours.

19. The method of claim 15, wherein the vasopressor is vasopressin.

20. The method of claim 15, wherein the vasopressor is a catecholamine.

21. A method of treating a human patient suffering from refractory hypotension, comprising administering angiotensin II to the patient at a rate of about 5 ng/kg/min to about 20 ng/kg/min while the patient is receiving a vasopressor, wherein the vasopressor is vasopressin or a catecholamine.

22. The method of claim 21, wherein the Angiotensin II is administered to the patient over a period of from about 1 hour to about 7 hours.

23. The method of claim 21, wherein the Angiotensin II is administered to the patient over a period of from about 2 hours to about 6 hours.

24. The method of claim 21, wherein the Angiotensin II is administered to the patient over a period of from about 3 hours to about 5 hours.

25. The method of claim 21, wherein the vasopressor is vasopressin.

26. The method of claim 21, wherein the vasopressor is a catecholamine.

27. The method of claim 26, wherein the catecholamine is norepinephrine.

28. The method of claim 27, wherein the norepinephrine is administered to the patient at a rate of >15 mcg/min.

\* \* \* \* \*